(12) United States Patent
Datta et al.

(10) Patent No.: US 12,426,841 B2
(45) Date of Patent: Sep. 30, 2025

(54) SYSTEM AND METHOD FOR A LIDAR GUIDED PATIENT POSITIONING APPARATUS FOR A COMPUTED TOMOGRAPHY SYSTEM

(71) Applicant: GE Precision Healthcare LLC, Waukesha, WI (US)

(72) Inventors: Arka Datta, Pewaukee, WI (US); Brian Edward Nett, Wauwatosa, WI (US); Chelsey Amanda Lewis, Waukesha, WI (US); John Moore Boudry, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 197 days.

(21) Appl. No.: 18/469,149

(22) Filed: Sep. 18, 2023

(65) Prior Publication Data
US 2025/0090110 A1    Mar. 20, 2025

(51) Int. Cl.
*A61B 6/03* (2006.01)
*A61B 6/00* (2006.01)
(Continued)

(52) U.S. Cl.
CPC ............ *A61B 6/035* (2013.01); *A61B 6/0428* (2013.01); *A61B 6/4241* (2013.01); *A61B 6/4447* (2013.01); *A61B 6/461* (2013.01)

(58) Field of Classification Search
CPC ..... A61B 6/035; A61B 6/0428; A61B 6/4241; A61B 6/4447; A61B 6/461; A61B 6/032;
(Continued)

(56) References Cited

U.S. PATENT DOCUMENTS 8,417,315 B2    4/2013  Mostafavi et al.
8,939,920 B2    1/2015  Maad
(Continued)

FOREIGN PATENT DOCUMENTS

DE    102014205702    10/2015
WO    2015134521    9/2015

OTHER PUBLICATIONS

Manava et al., "Optimized Camera-Based Patient Positioning in CT Impact on Radiation Exposure," Investigative Radiology, vol. 58, No. 2, Feb. 2023, 5 pgs.

*Primary Examiner* — Kiho Kim
(74) *Attorney, Agent, or Firm* — Fletcher Yoder, P.C.

(57) ABSTRACT

A method includes receiving data acquired with a light detection and ranging (LiDAR) scanning system physically coupled to a computed tomography (CT) imaging system of a subject to be imaged disposed on a cradle of a table, wherein the table is configured to move the subject into and out of a bore of a gantry of the CT imaging system. The method also includes generating a multi-dimensional avatar of the subject representing a topography of the subject. The method further includes causing display of the multi-dimensional avatar positioned on the cradle that represents a current position of the subject on the display, wherein the display is disposed adjacent the table within view of the subject. The method even further includes providing instructions on the display to enable the subject to guide themselves to a target position on the cradle for a CT scan with the CT imaging system.

20 Claims, 14 Drawing Sheets

(51) Int. Cl.
*A61B 6/04* (2006.01)
*A61B 6/42* (2024.01)
*A61B 6/46* (2024.01)

(58) Field of Classification Search
CPC ... A61B 6/0407; A61B 6/0487; A61B 6/0492; A61B 6/08; A61B 6/465
See application file for complete search history.

(56) References Cited

U.S. PATENT DOCUMENTS

| | | |
|---|---|---|
| 10,376,217 B2 | 8/2019 | Schmidt et al. |
| 11,107,270 B2 | 8/2021 | Kirchberg et al. |
| 11,207,035 B2 | 12/2021 | Eibenberger et al. |
| 11,276,166 B2 | 3/2022 | Prasad et al. |
| 11,547,323 B2 | 1/2023 | Pai et al. |
| 2010/0074497 A1* | 3/2010 | Mielenz ............. A61B 6/032 382/128 |
| 2020/0258243 A1* | 8/2020 | Chang ............... A61B 5/107 |
| 2020/0260066 A1* | 8/2020 | Liu .................. A61B 90/37 |
| 2021/0110594 A1 | 4/2021 | Teixeira et al. |
| 2021/0251516 A1 | 8/2021 | Pai et al. |
| 2024/0366162 A1* | 11/2024 | Young ............... A61B 6/505 |

\* cited by examiner

SYSTEM AND METHOD FOR A LIDAR GUIDED PATIENT POSITIONING APPARATUS FOR A COMPUTED TOMOGRAPHY SYSTEM

BACKGROUND

The subject matter disclosed herein relates to medical imaging systems and, more particularly, to a light detection and ranging or laser imaging, detection, and ranging (LiDAR) guided patient positioning apparatus for a computed tomography (CT) imaging system.

In CT, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a patient's body. In CT systems a detector array, including a series of detector elements or sensors, produces similar signals through various positions as a gantry is displaced around a patient, allowing volumetric reconstructions to be obtained.

In certain scenarios, a patient to be imaged may be sick with a highly contagious disease. It would be useful for a technologist to not go into the scan room in order to assist in positioning the patient for the CT scan to avoid the technologist becoming infected. Therefore, there is a need for a way to enable the patient to be properly positioned for the CT scan without exposing the technologist to a highly contagious disease.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a medical imaging system is provided. The medical imaging system includes a CT imaging system. The CT imaging system includes a gantry having a bore, rotatable about an axis of rotation. The CT imaging system also includes a table configured to move a subject to be imaged into and out of the bore of the gantry, a radiation source mounted on the gantry and configured to emit an X-ray beam, and a detector configured to detect the X-ray beam emitted by the radiation source. The medical imaging system also includes a display disposed adjacent the table within view of the subject. The medical imaging system further includes a LiDAR scanning system physically coupled to the CT imaging system. The LiDAR scanning system is configured to acquire data of the subject from different angular positions relative to the axis of rotation. The medical imaging system further includes processing circuitry configured to receive the data acquired with the LiDAR scanning system, to generate a multi-dimensional avatar of the subject representing a topography of the subject, to cause display of the multi-dimensional avatar positioned on the cradle that represents a current position of the subject on the display, and to provide instructions on the display to enable the subject to guide themselves to a target position on the cradle for a CT scan with the CT imaging system.

In another embodiment, a computer-implemented method is provided. The computer-implemented method includes receiving, at a processor, data acquired with a light detection and ranging (LiDAR) scanning system physically coupled to a computed tomography (CT) imaging system of a subject to be imaged disposed on a cradle of a table, wherein the table is configured to move the subject into and out of a bore of a gantry of the CT imaging system. The computer-implemented method also includes generating, via the processor, a multi-dimensional avatar of the subject representing a topography of the subject. The computer-implemented method further includes causing, via the processor, display of the multi-dimensional avatar positioned on the cradle that represents a current position of the subject on a display, wherein the display is disposed adjacent the table within view of the subject. The computer-implemented method even further includes providing, via the processor, instructions on the display to enable the subject to guide themselves to a target position on the cradle for a CT scan with the CT imaging system.

In a further embodiment, a non-transitory computer-readable medium, the computer-readable medium including processor-executable code that when executed by a processor, causes the processor to perform actions. The actions include receiving data acquired with a light detection and ranging or laser imaging, detection, and ranging (LiDAR) scanning system physically coupled to a computed tomography (CT) imaging system of a subject to be imaged disposed on a cradle of a table, wherein the table is configured to move the subject into and out of a bore of a gantry of the CT imaging system. The actions also include generating a multi-dimensional avatar of the subject representing a topography of the subject. The actions further include causing display of the multi-dimensional avatar positioned on the cradle that represents a current position of the subject on a display, wherein the display is disposed adjacent the table within view of the subject. The actions even further include providing instructions on the display to enable the subject to guide themselves to a target position on the cradle for a CT scan with the CT imaging system.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
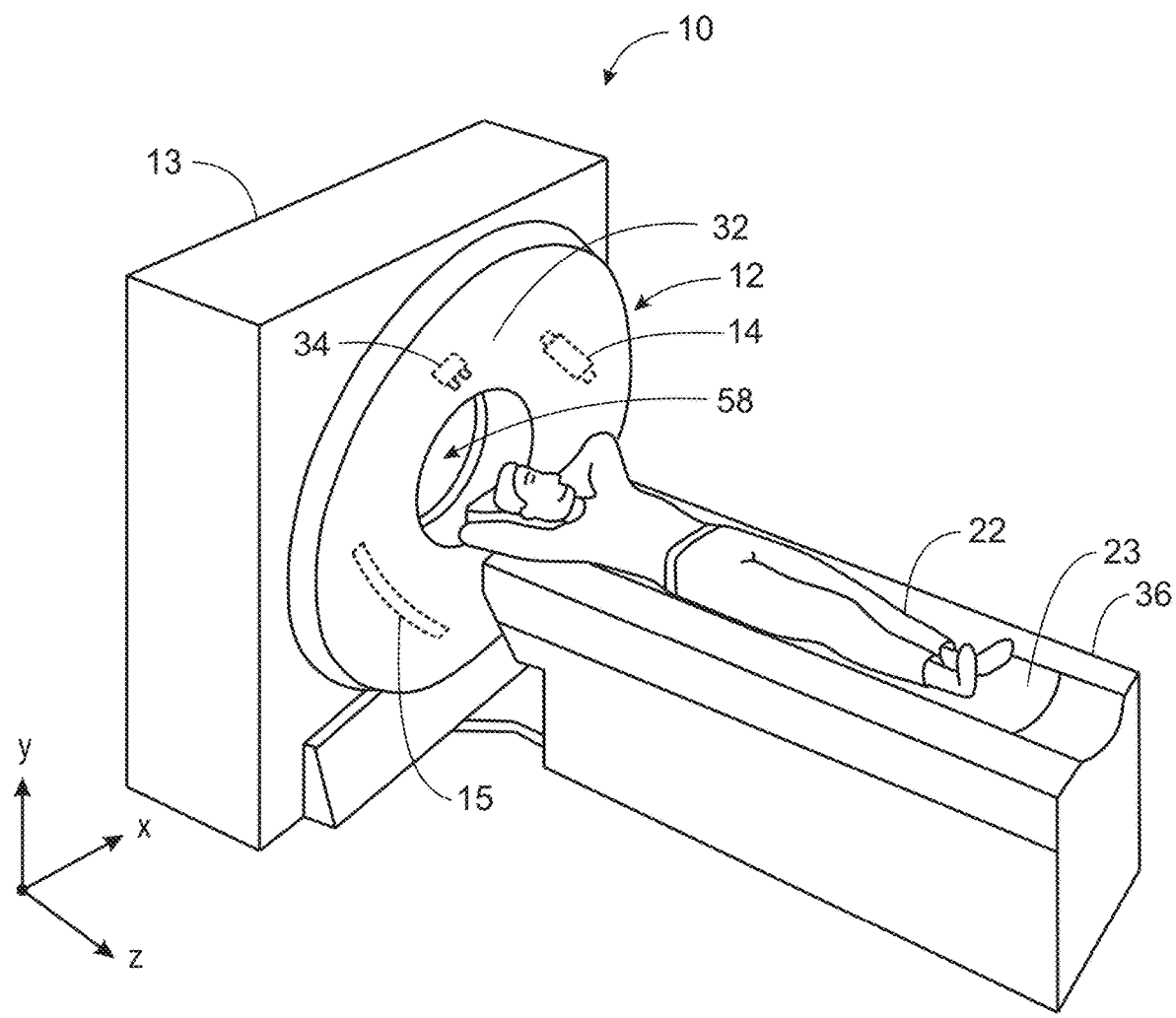
FIG. 1 is a pictorial representation of a CT imaging system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context to provide accurate 3D information of a target to improving workflow processes and post processing steps.

The present disclosure provides systems and methods for incorporating LiDAR based techniques with a CT imaging system to aid various workflows more efficiently. A LiDAR system is a remote sensing method to measure target objects a variable distance from a source. With the advancement of LiDAR technique, it can now produce 3D rendering of a subject with high spatial resolution (e.g., sub millimeter (mm) accuracy). The disclosed techniques do not need any X-ray radiation to image the target or patient and only require time of flight information of reflected pulsed light (e.g., laser) to calculate and reproduce 3D information (e.g., depth dependent information) of the patient. Multiple views are utilized to cover an entire target area to reproduce high fidelity 3D information. In certain embodiments, light images may be acquired by moving the data acquisition system (i.e., LiDAR scanning system having one or more LiDAR scanners or instruments) across the target (e.g., along the gantry). In this embodiment, the data acquisition system may be integrated outside the scan window (and, thus, physically coupled to the CT system) and rotated to capture multiple views. In certain embodiments, multiple LiDAR scanners or instruments may be placed across different angular positions around the patient to capture the entire region of interest.

The LiDAR-based data may be acquired prior to a CT scan of the target or patient. The LiDAR-based data may be utilized as part of a patient positioning apparatus for a CT scan. In particular, processing circuitry may be configured to receive the data acquired with the LiDAR scanning system, to generate a multi-dimensional—dimensional (e.g., two-dimensional (2D) or three-dimensional (3D)) avatar of the subject (e.g., patient) representing a topography of the subject, to cause display of the avatar positioned on the cradle that represents a current position of the subject on a display (e.g., external display coupled to housing of the gantry, the ceiling in the scan room, etc.), and to provide instructions on the display to enable the subject to guide themselves to a target position on the cradle for a CT scan with the CT imaging system. In certain embodiments, the processing circuitry is configured to provide instructions by causing display of (e.g., an image of) the multi-dimensional avatar in a target position positioned on the cradle on the display alongside the multi-dimensional avatar positioned on the cradle in the current position. In certain embodiments, instructions may be provided via automatic voice commands, visible light, or haptic cues. In certain embodiments, the processing circuitry is further configured to perform template matching between the current position of the subject and the target position. In certain embodiments, the processing circuitry is further configured to provide a user-perceptible indication as to whether the current position of the subject and the target position match. In certain embodiments, the user-perceptible indication is provided via color coding of a shape (e.g., rectilinear shape such as a box) on the display disposed around the avatar positioned on the cradle in the current position. For example, the shape may be displayed in a first color when the current position of the subject and the target position match. The shape may also be displayed in a second color (different from the first color) when the current position of the subject and the target position do not match. In certain embodiments, the user-perceptible indication is a directional arrow shown on the display to assist to the subject to achieve the target position. In certain embodiments, the processing circuitry is configured to provide additional instructions to the subject to hold the current position for the CT scan when the current position of the subject and the target position do not match. In certain embodiments, the processing circuitry is configured to determine the target position based on a scan protocol for the CT scan. It should be noted that the information provided by LiDAR-based data can be utilized in other workflows (e.g., automatically adjusting a table height based on isocenter offset for scanning a patient or a calibration phantom).

The LiDAR guided patient positioning apparatus guides and assists the subject to position themselves. In particular, the LiDAR-based data is utilized to guide a subject within an interactive virtual visual apparatus to improve overall efficiency and the robustness of the workflow in utilizing a CT scanner. The LiDAR-based data generates high-fidelity positional 3D data without any marker or pattern projected on the subject. Thus, data can be collected effortlessly and the 3D point cloud information can be efficiently used to improve the robustness of the CT data acquisition workflow process. This also enables the technologist to be out of the scan room during patient positioning, thus, reducing the potential spread of any contagious disease the subject may have. The automated table adjustment feature also ensures dose optimization and automated phantom adjustment during calibration. The disclosed embodiments provide for effortless, efficient workflow and/or dose optimization.

Figure 2:
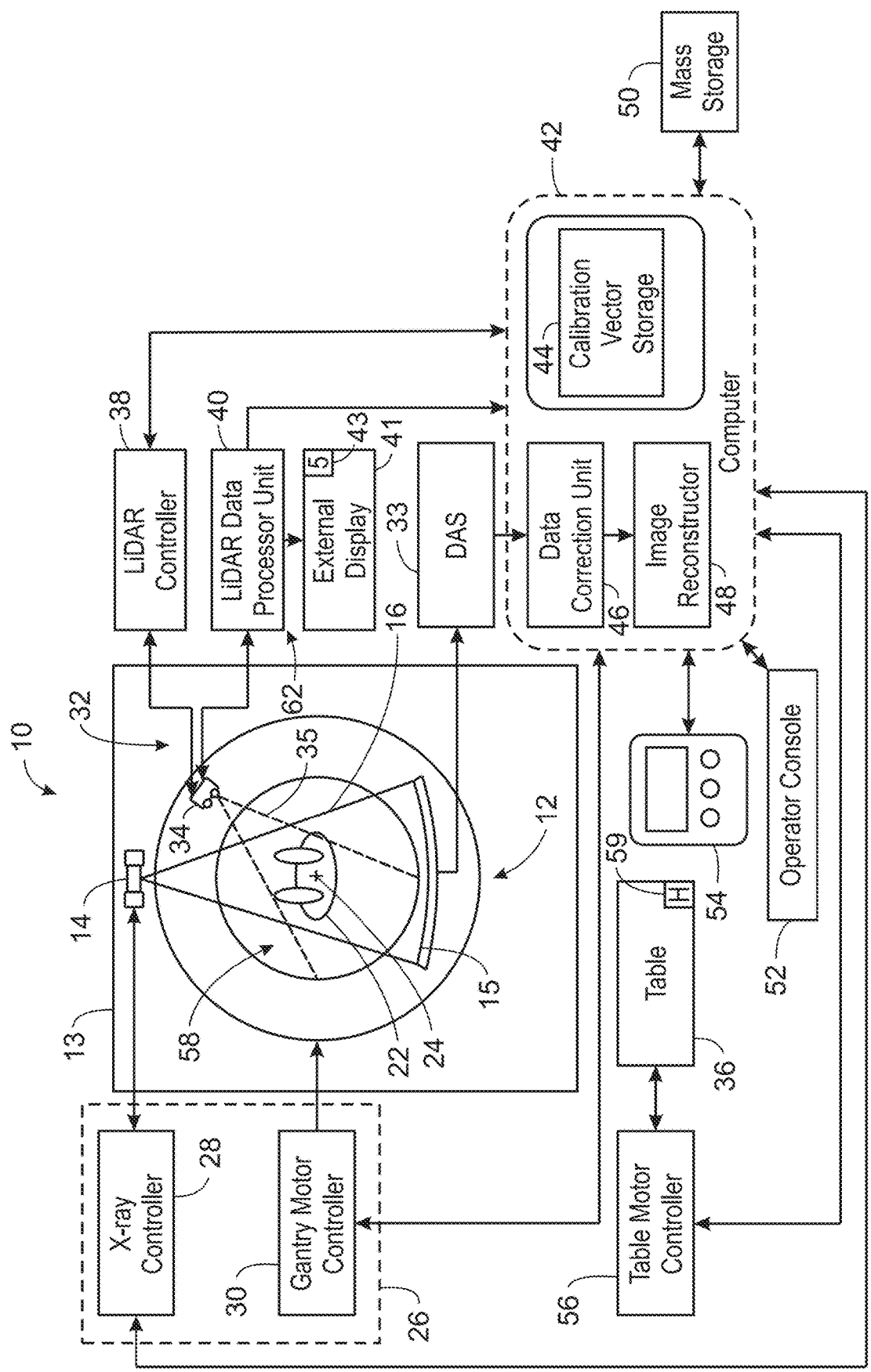
FIG. 2 is a block diagram of the CT imaging system in FIG. 1, in accordance with aspects of the present disclosure.

With the preceding in mind and referring to FIGS. 1 and 2, a CT imaging system 10 is shown, by way of example. The CT imaging system 10 includes a gantry 12 coupled to a housing 13 (e.g., gantry housing). The gantry 12 has a rotating component and a stationary component. The gantry 12 has an X-ray source 14 that projects a beam of X-rays 16 toward an X-ray detector assembly or X-ray detector array 15 (e.g., having a plurality of detector modules) on the opposite side of the gantry 12. The X-ray source 14 and the X-ray detector assembly 15 are disposed on the rotating portion of the gantry 12. The X-ray detector assembly 15 is coupled to data acquisition systems (DAS) 33. The plurality of detector modules of the X-ray detector assembly 15 detect the projected X-rays that pass through a patient or subject 22 (disposed on a cradle 23 of a table 36), and DAS 33 converts the data to digital signals for subsequent processing. Each detector module of the X-ray detector assembly 15 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 (e.g., isocenter) so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to the X-ray source 14 and a gantry motor controller 30 that controls the rotational speed and position of gantry 12.

The imaging system 10 also includes a light detection and ranging (LiDAR) scanning system 32 physically coupled to the imaging system 10. The LiDAR scanning system 32 includes one or more LiDAR scanners or instruments 34. As depicted, the LiDAR scanning system 32 has one LiDAR scanner 34. The one or more LiDAR scanners 34 are utilized to acquire depth dependent information (LiDAR data or light images) of the patient 22 with high spatial fidelity. The depth dependent information is utilized in subsequent workflow processes for a CT scan. The one or more LiDAR scanners 34 emit pulsed light 35 (e.g., laser) at the patient 22 and detect the reflected pulsed light from the patient 22. The LiDAR scanning system 32 is configured to acquire the LiDAR data from multiple different views (e.g., at different angular positions relative to the axis of rotation 24).

In certain embodiments, as depicted in FIGS. 1 and 2, the LiDAR scanner 34 is coupled to the gantry 12. In particular, the LiDAR scanner 34 is disposed within the gantry housing 13 outside a scan window. The LiDAR scanner 34 is rotated across the patient 22 to acquire the LiDAR data at the different angular positions. In certain embodiments, multiple LiDAR scanners 34 may be coupled to the gantry 12 and rotated to acquire the LiDAR data at the different angular positions.

In certain embodiments, multiple LiDAR scanners 34 may be coupled to the gantry 12 in fixed positions but disposed at different angular positions (e.g., relative to axis of rotation 24). The LiDAR scanners 34 in fixed positions may acquire the LiDAR data at the same time while remaining stationary.

In certain embodiments, the LiDAR scanning system 32 may be external to the gantry 12 but still physically coupled to the imaging system 10. For example, multiple LiDAR scanners 34 may be coupled to a LiDAR panel (e.g., at different angular positions relative to the axis of rotation 24) that is coupled to a guide rail system. The guide rail system may be coupled to the gantry housing 13 or a table 36 of the system 10. The guide rail system may be configured to move the LiDAR panel toward and away from the gantry 12. In certain embodiments, the guide rail system may also be configured to rotate the LiDAR panel about the axis of rotation 24.

The LiDAR scanning system 32 includes a LiDAR controller 38 configured to provide timing and control signals to the one or more LiDAR scanners 34 for acquiring the LiDAR data at the different angular positions. The LiDAR data may be acquired prior to, during, and/or subsequent to a CT scan of the patient 22. The LiDAR scanning system 32 also includes a LiDAR data processing unit 40 that receives or obtains the LiDAR data from the one or more LiDAR scanners 34. The LiDAR data processing unit 40 utilizes time of flight information of the reflected pulsed light and processes the LiDAR data (e.g., acquired at the different views) to generate an accurate 3D measurement of the patient 22. The 3D measurement of the patient 22 has a high spatial resolution (e.g., sub mm accuracy). As noted above, the 3D measurement may be utilized in subsequent workflow processes of a CT scan as described in greater detail below. A display 41 (e.g., external display) is coupled to the LiDAR data processor unit 40. The display 41 is disposed adjacent to the table 36 within view of the patient 22. In certain embodiments, the display 41 is coupled to the gantry housing 13. In certain embodiments, the display 41 is coupled to a ceiling or somewhere else within the scan room. In certain embodiments, the display 41 includes a speaker 43 for providing automatic voice instructions to help the patient 22 guide themselves. In certain embodiments, the speaker 43 may be separate from the display and disposed at another location within the scan room.

The 3D measurement information from the LiDAR scanning system 32 (e.g., from the LiDAR data processing unit 40) and the scan data from the DAS 33 is input to a computer 42. The computer 42 includes a calibration vector storage 44 (e.g., for storing calibration parameters and calibration protocols for acquiring the CT scan data). The 3D measurement information obtained from the LiDAR scanning system 32 may be utilized in determining the calibration parameters utilized. The computer 42 also includes a data correction unit 46 for processing or correcting the CT scan data from the DAS 33. The computer 42 further includes an image reconstructor 48. The image reconstructor 48 receives sampled and digitized X-ray data from DAS 33 and performs high-speed reconstruction. The reconstructed image is applied as an input to the computer 42, which stores the image in a mass storage device 50. Computer 42 also receives commands and scanning parameters from an operator via console 52. An associated display 54 allows the operator to observe the reconstructed image as well as the 3D measurement data and other data from the computer 42. The operator supplied commands and parameters are used by computer 42 to provide control signals and information to the DAS 33, X-ray controller 28, gantry motor controller 30, and the LiDAR controller 38. In addition, computer 42 operates a table motor controller 56, which controls a motorized table 36 to position the patient 22 relative to the gantry 12. Particularly, table 36 moves portions of the patient 22 (via the cradle 23 that supports the patient 22) through a gantry opening or bore 58. In certain embodiments, the table 36 may include haptic transducers 59 to help guide the patient 22 position themselves for a scan. For example, a short vibration felt by the patient 22 via the haptic transducers 59 may indicate an improper position for a scan while a long vibration may an indicate a proper position or vice versa.

The computer 42 and the LiDAR processor unit 40 include may each include processing circuitry. The processing circuitry may be one or more general or application-specific microprocessors. The processing circuitry may be configured to execute instructions stored in a memory to perform various actions. For example, the processing circuitry may be utilized for receiving or obtaining LiDAR data acquired with the LiDAR scanning system 32. In addition, the processing circuitry may also generate a 3D measurement of the patient 22. Further, the processing circuitry may utilize the 3D measurement in a subsequent workflow process for a CT scan of the patient with the CT imaging system 32.

For example, the processing circuitry is configured to receive the data acquired with the LiDAR scanning system 32 of the patient 22, to generate a multi-dimensional (e.g., 2D or 3D) avatar of the patient 22 representing a topography of the subject (e.g., from the LiDAR-based data), to cause display of the multi-dimensional avatar positioned on the cradle 23 that represents a current position (e.g., current body posture) of the patient 22 on the display 41, and to provide instructions on the display 41 to enable the patient 22 to guide themselves to a target position (target body posture) on the cradle for a CT scan with the CT imaging system. In certain embodiments, the processing circuitry is configured to provide instructions by causing display (e.g., of an image) of the multi-dimensional avatar in a target position positioned on the cradle 23 on the display 41 alongside the multi-dimensional avatar positioned on the cradle 23 in the current position. In certain embodiments, instructions may be provided via automatic voice commands, visible light, or haptic cues. In certain embodiments, the processing circuitry is further configured to perform template matching between the current position of the patient 22 and the target position. In certain embodiments, the processing circuitry is further configured to provide a user-perceptible indication as to whether the current position of the patient 22 and the target position match. In certain embodiments, the user-perceptible indication is provided via color coding of a shape (e.g., rectilinear shape such as a box) on the display 41 disposed around the avatar positioned on the cradle 23 in the current position. For example, the shape may be displayed in a first color when the current position of the patient 22 and the target position match. The shape may also be displayed in a second color (different from the first color) when the current position of the subject and the target position do not match. In certain embodiments, the user-perceptible indication is a directional arrow shown on the display 41 to assist to the patient 22 to achieve the target position. In certain embodiments, the processing circuitry is configured to provide additional instructions to the patient 22 to hold the current position for the CT scan when the current position of the patient 22 and the target position do not match. In certain embodiments, the processing circuitry is configured to determine the target position based on a scan protocol for the CT scan. The components of the LiDAR scanning system 32 and the display 41 (and in certain embodiments, the haptic transducers 59) form a LiDAR guided patient positioning apparatus 62. It should be noted that the information provided by LiDAR-based data can be utilized in other workflows (e.g., automatically adjusting a table height based on isocenter offset for scanning a patient or a calibration phantom).

In certain embodiments, the processing circuitry may be utilized in adjusting a height of the table 36 to align an isocenter of the gantry 12 with a center of a region of interest of a target (e.g., the patient 22 or a phantom). For example, in certain embodiments, the processing circuitry is configured to landmark a target disposed on the cradle 23 of the table 36 of the CT imaging system 10 outside the bore 58 of the gantry 12. In certain embodiments, the processing circuitry is configured to perform a LiDAR scan on the target. The LiDAR scan is performed utilizing the LiDAR scanning system 32. The LiDAR scan is performed prior to a CT scan (e.g., calibration scan or diagnostic scan).

In certain embodiments, the processing circuitry is configured to obtain or receive LiDAR data from the LiDAR scan. The LiDAR data represents light images of different views acquired at different angular positions (e.g., relative to axis of rotation 24). In certain embodiments, the processing circuitry is configured to process the LiDAR data.

In certain embodiments, the processing circuitry is configured to perform segmentation on the 3D information (3D point cloud data) to generate 3D point cloud information of the target. In certain embodiments, the segmentation of the 3D information is performed utilizing density based spatial clustering of applications with noise (DBSCAN). The 3D point cloud information of the patient represents a high fidelity topography of the target.

In certain embodiments, the processing circuitry is configured to estimate a center of a region of interest of the target. Estimating the center of the region of interest may include setting landmarks as needed and isolating the region of interest from the segmented 3D information of the target. The isolated region of interest may be a two-dimensional (2D) contour representation for a selected surface of the region of interest. The center of region of interest may be determined from the 2D contour representation of the region of interest of the target. In certain embodiments, estimating the center of region of interest of the target includes estimating a center of mass attenuation of a region of interest of a patient. In this embodiment, upon isolating the region of interest (2D contour representation) a location of the region of interest may be determined from an anatomical model. The anatomical model may be utilized to estimate the center of the mass attenuation of the patient. In certain embodiments, the anatomical model is scaled using the LiDAR data.

In certain embodiments, the processing circuitry is configured to obtain isocenter coordinate information from the CT imaging system 10. The isocenter coordinate information includes an isocenter of the gantry 12. In certain embodiments, the processing circuitry is configured to calculate an offset between the center of the region of interest of the target and isocenter of the gantry 12.

In certain embodiments, the processing circuitry is configured to provide a prompt (e.g., on a console (e.g., display) of the CT imaging system 10) to the operator to adjust a height of the table 36 by the determined offset to align the isocenter of the gantry 12 with the center of region of interest of the target. In response, the processing circuitry receives an input to adjust the height of the table 36 from the operator via an input device of the console. In certain embodiments, the processing circuitry is configured to automatically move the table 36 (i.e., adjust the height of the table) 36 by the determined offset to align the isocenter of the gantry 12 with the center of region of interest of the target. Adjusting the height of the table 36 to align the isocenter of the gantry 12 with the center of region of interest of the target (e.g., the patient 22) improves dose optimization.

In certain embodiments, upon adjusting the table, the processing circuitry is configured to start the scan. In certain embodiments, the scan is CT diagnostic scan of a patient. In certain embodiments, the scan is a CT calibration scan utilizing a phantom.

Figure 3:
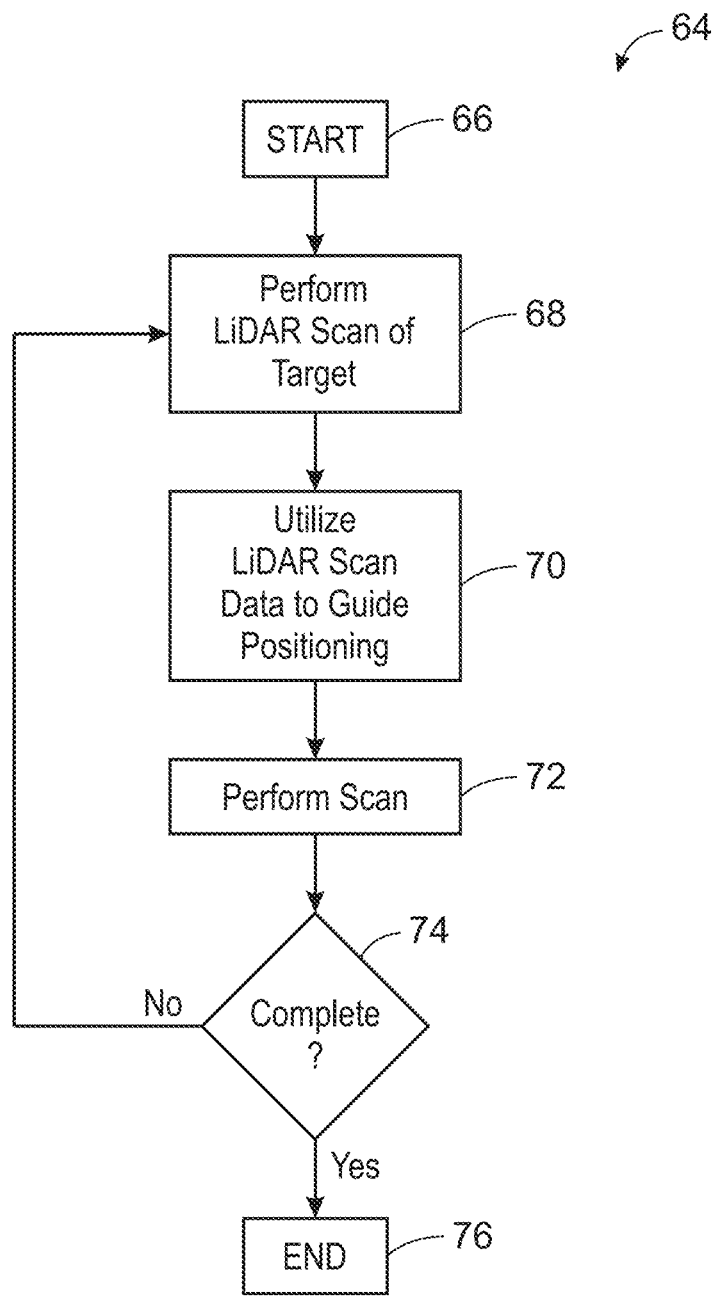
FIG. 3 is a flowchart of a method for acquiring and utilizing LiDAR data for positioning, in accordance with aspects of the present disclosure.

FIG. 3 is a flowchart of a method 64 for acquiring and utilizing LiDAR data for positioning. The method 64 may be performed by one or more components (e.g., processing circuitry) of the LiDAR scanning system 32 and/or the CT imaging system 10 in FIGS. 1 and 2. One or more steps of the method 64 may be performed simultaneously and/or in a different order than depicted in FIG. 3.

Upon starting the method 64 (block 66), the method 64 includes performing a LiDAR scan (e.g., utilizing the LiDAR scanning system 32 in FIGS. 1 and 2) of a target (e.g., patient or phantom) (block 68). The LiDAR scan is performed while the target is positioned on the cradle of CT table of the CT imaging system. The LiDAR scan occurs prior to a scan.

The method 64 also includes utilizing the LiDAR-based data of the target to guide positioning of the target (block 70). The LiDAR-based data is processed (e.g., segmented and tracked) in real time (e.g., virtually immediately as the data is collected or acquired) to create a 3D point cloud representing a high fidelity topography of the target. The 3D point cloud contains real time positional information. In certain embodiments, this real time positional information of the 3D point cloud data can be processed and viewed in real time interactively to guide a patient to position themselves for a subsequent scan. In certain embodiments, the 3D point cloud data can be utilized to identify the center of the target to calculate an offset from the isocenter and the adjust a table height accordingly.

Upon utilizing the LiDAR-based data to guide positioning of the target, the method 64 includes performing a scan (block 72). The scan may be a CT diagnostic scan or CT calibration scan. The method 64 includes determining if the process is complete (block 74). If the process is not complete, the method 64 returns to performing the LiDAR scan of the target (block 68). If the process is complete, the method 64 ends (block 76).

Figure 4:
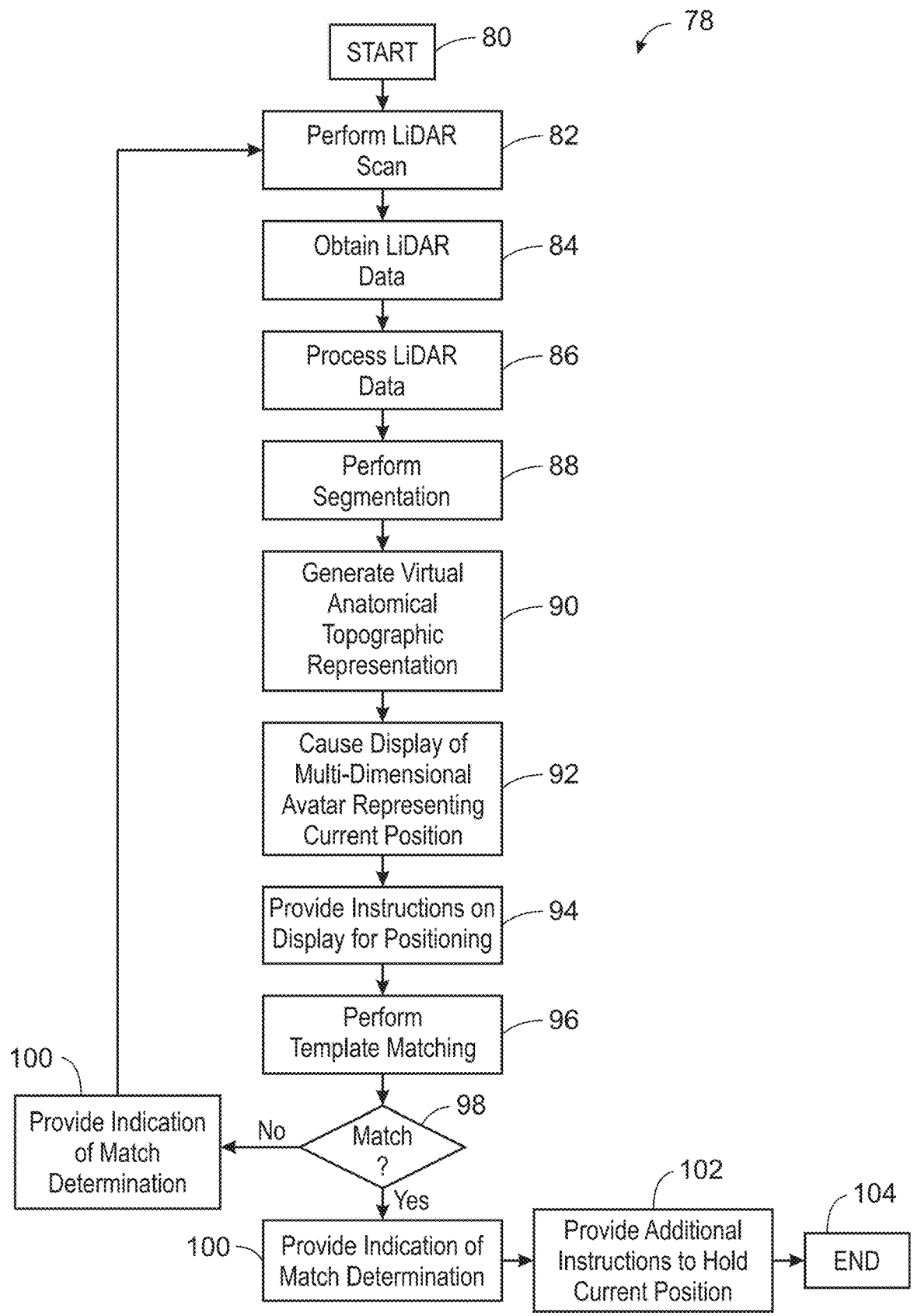
FIG. 4 is a flowchart of a method for acquiring and utilizing LiDAR for patient positioning (e.g., using an external display), in accordance with aspects of the present disclosure.

FIG. 4 is a flowchart of a method 78 for acquiring and utilizing LiDAR for patient positioning (e.g., using an external display). The method 78 may be performed by one or more components (e.g., processing circuitry) of the LiDAR scanning system 32 and/or the CT imaging system 10 in FIGS. 1 and 2. One or more steps of the method 78 may be performed simultaneously and/or in a different order than depicted in FIG. 4.

Upon starting the method 78 (block 80), the method 78 includes performing a LiDAR scan on a patient (e.g., subject) disposed on a cradle of a table of a CT imaging system outside the bore of the gantry (block 82). The LiDAR scan is performed utilizing the LiDAR scanning system 32 described in FIGS. 1 and 2. The LiDAR scan is performed prior to a CT scan (e.g., calibration scan or diagnostic scan).

The method 78 also includes obtaining or receiving LiDAR data from the LiDAR scan (block 84). The LiDAR data represents light images of different views acquired at different angular positions (e.g., relative to axis of rotation 24 in FIG. 2). The method 78 further includes processing the LiDAR data (block 86). Processing the LiDAR includes combining the LiDAR data and generating 3D information (i.e., 3D measurement) such as 3D point cloud data of the patient. Processing of the LiDAR data may also include changing a coordinate system, inspecting point components and values, tiling the LiDAR data, clipping points outside a defined boundary, reducing the number of points, splitting by component value, filtering the LiDAR data, and/or other processing techniques. These processing techniques may be performed prior to and/or after the generation of the 3D information.

The method 78 further includes performing segmentation on the multi-dimensional information (e.g., 3D point cloud data) to generate 3D point cloud information of the patient (block 88). In certain embodiments, the segmentation of the 3D information is performed utilizing density based spatial clustering of applications with noise (DBSCAN). The 3D point cloud information of the patient represents a high fidelity topography of the patient. The 3D point cloud information of the patient contains real time positional information which can be processed and viewed in real time to interactively guide a patient to position themselves for a CT scan. The method 78 still further includes generating a virtual anatomical topographic representation (e.g., multi-dimensional avatar) of the patient (block 90).

The method 78 also includes causing display of (in real time) the multi-dimensional avatar positioned on the cradle that represents a current (real time) position (e.g., current posture) of the patient on an external display within view of the patient (e.g., display 41 in FIGS. 2 and FIGS. 5-9) (block 92). The method 78 further includes providing instructions on the display to enable the patient to guide themselves to a target position (e.g., target posture) on the cradle for the CT scan (block 94). In certain embodiments, the target position is determined based on the scan protocol for the upcoming CT scan. In certain embodiments, providing instructions on the display includes causing display of the multi-dimensional avatar in the target position on the cradle on the display alongside (e.g., side by side) the multi-dimensional avatar positioned on the cradle in the current position. In certain embodiments, these on-screen instructions may be accompanied by automatic audio instructions (e.g., via a speaker associated with the external display or somewhere else within the scan room) to guide the patient in positioning themselves. In certain embodiments, these on-screen instructions may be accompanied visible light cues to guide the patient in positioning themselves (e.g., via LED lights associated with the table, the CT scanner, and/or within the scan room). In certain embodiments, these on-screen instructions may be accompanied by haptic cues or signals provided by haptic transducers within the table the patient is disposed on to guide the patient in positioning themselves. In certain embodiments, one or more these automatic voice commands, visible light cues, and haptic cues may be provided in combination with the on-screen instructions or instead of the on-screen instructions.

The method 78 includes performing template matching between the current (real time) position of the patient and the target position (block 96). The method 78 includes determining if there is a match (i.e., the current position matches the target position) (block 98). Whether there is a match or not, the method 78 includes providing a user-perceptible indication as whether the current position of the patient and the target position match (block 100). In certain embodiments, the user-perceptible indication is provided via color coding of a shape (e.g., rectilinear shape such as a box) on the display that is disposed about the multi-dimensional avatar positioned on the cradle in the current position. In certain embodiments, the shape is displayed in a first color (e.g., green) when the current position of the patient and the target position match, while the shape is displayed in a second color (e.g., red) when the current position of the patient and the target position do not match. In certain embodiments, the user-perceptible indication is a directional arrow shown on the display to assist to the subject to achieve the target position. In addition, or alternatively, one or more of automatic voice commands, visible light cues, and/or haptic cues may be utilized to provide an indication as to whether the current position of the patient and the target position match. Besides providing the user-perceptible indication related to the match, when the current position of the patient and the target position do not match, the method 78 returns to performing the LiDAR scan and repeating the method 78 (block 82). Besides providing the user-perceptible indication, when the current position of the patient and the target position match, the method 78 includes providing additional instructions to the patient to hold the current position for the CT scan as the scan will start (block 102). The additional instructions may be provided on-screen of the external display or provided audibly. Upon providing these additional instructions, the method 78 ends (block 104).

Figure 5:
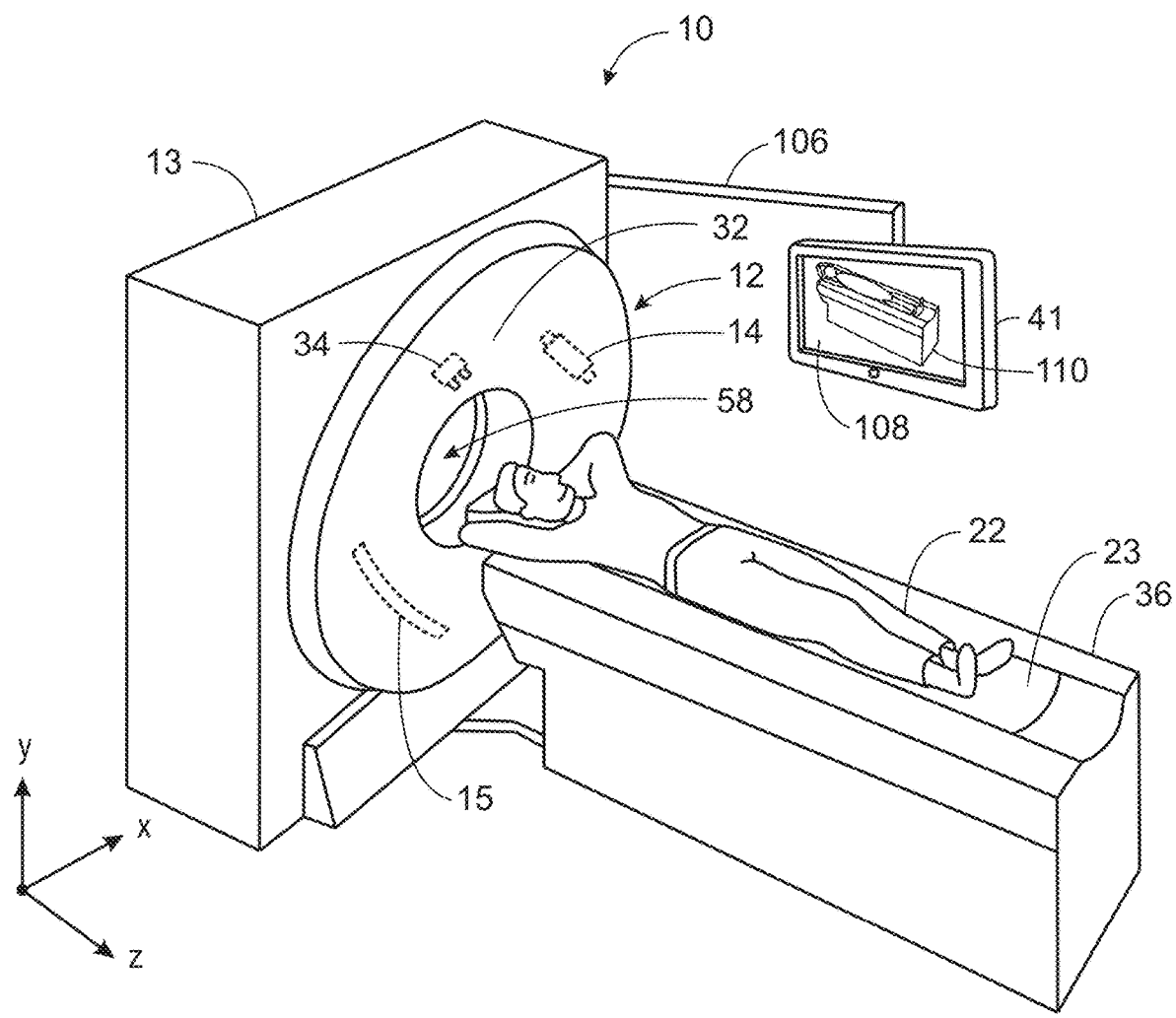
FIG. 5 is a schematic diagram of the CT imaging system in FIG. 1 coupled to an external display for providing patient positioning guidance, in accordance with aspects of the present disclosure.
Figure 6:
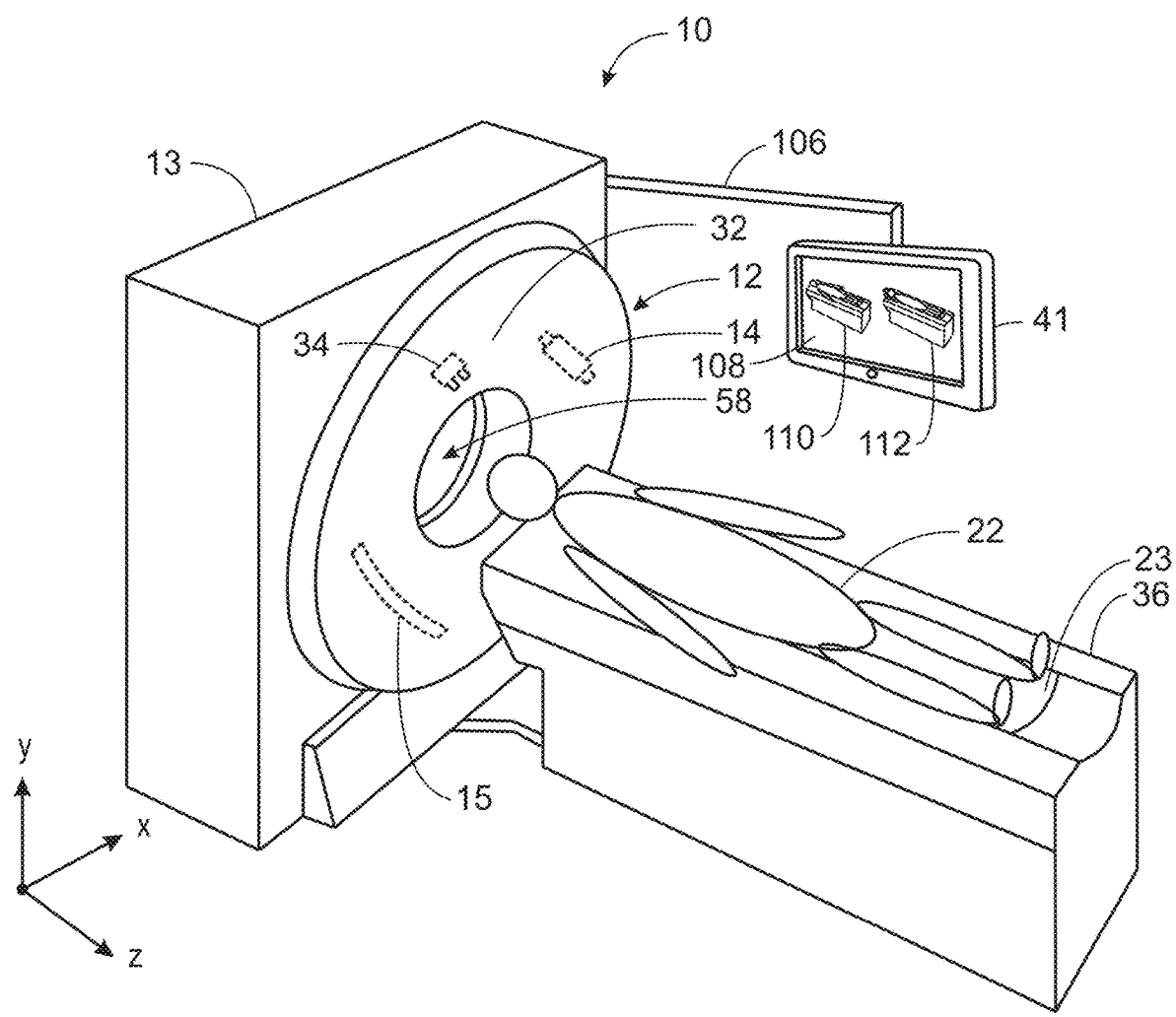
FIG. 6 is a schematic diagram of the CT imaging system in FIG. 6 displaying a current position and a target position of the patient on the external display, in accordance with aspects of the present disclosure.

FIG. 5 is a schematic diagram of the CT imaging system 10 in FIG. 1 coupled to an external display 41 (e.g., monitor) providing patient positioning guidance. The CT imaging system 10 is as described in FIGS. 1 and 2. As depicted in FIG. 5, the external display 41 is coupled to the gantry housing 13 via a mechanical arm 106. In certain embodiments, the display 41 not be coupled to CT imaging system 10. The patient 22 is disposed on the cradle 23 prior to the scan while the LiDAR scanning system 32 acquires LiDAR-based data of the patient 22. The LiDAR-based data is processed and utilized as described in the method 78 in FIG. 4. The display 41 is positioned so that a screen 108 of the display 41 is visible to the patient 22 on the cradle 23. As depicted in FIG. 5, a multi-dimensional avatar of the patient 22 disposed on the cradle 23 in a current (real time) position (represented by reference numeral 110) is shown on the screen 108 to provide guidance to the patient 22 in positioning themselves on the cradle 23. In certain embodiments, as depicted in FIG. 6, an image of the multi-dimensional avatar of the patient 22 disposed on the cradle 23 in a target position (represented by reference numeral 112) is shown on the screen 108 to provide further guidance. The image 112 representing the target position is disposed alongside (e.g., side by side) with the multi-dimensional avatar in the current position represented by reference numeral 110.

Figure 7:
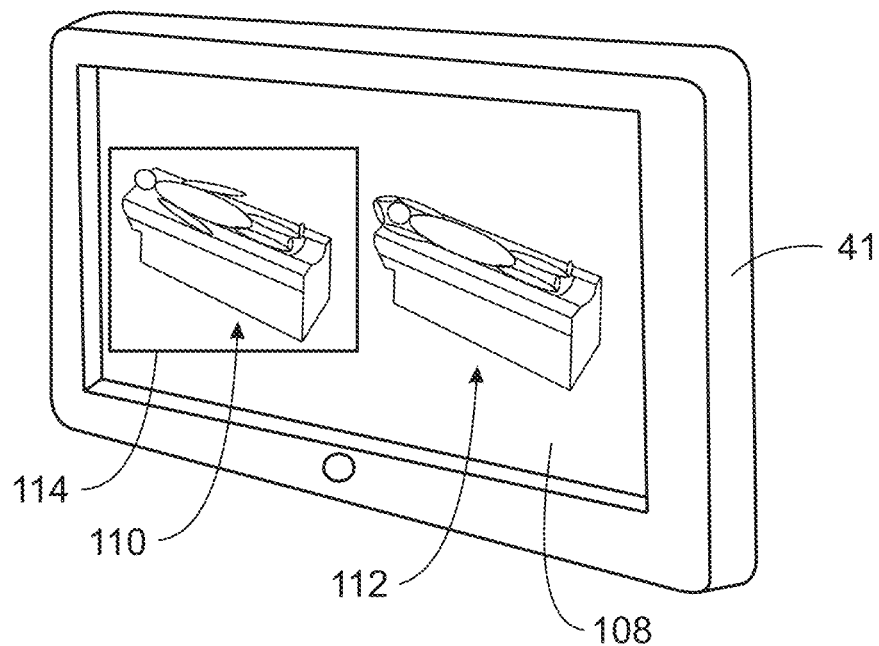
FIG. 7 is a schematic diagram of a screen on the external display of the CT imaging system providing positioning guidance (with the patient in a first incorrect position), in accordance with aspects of the present disclosure.
Figure 8:
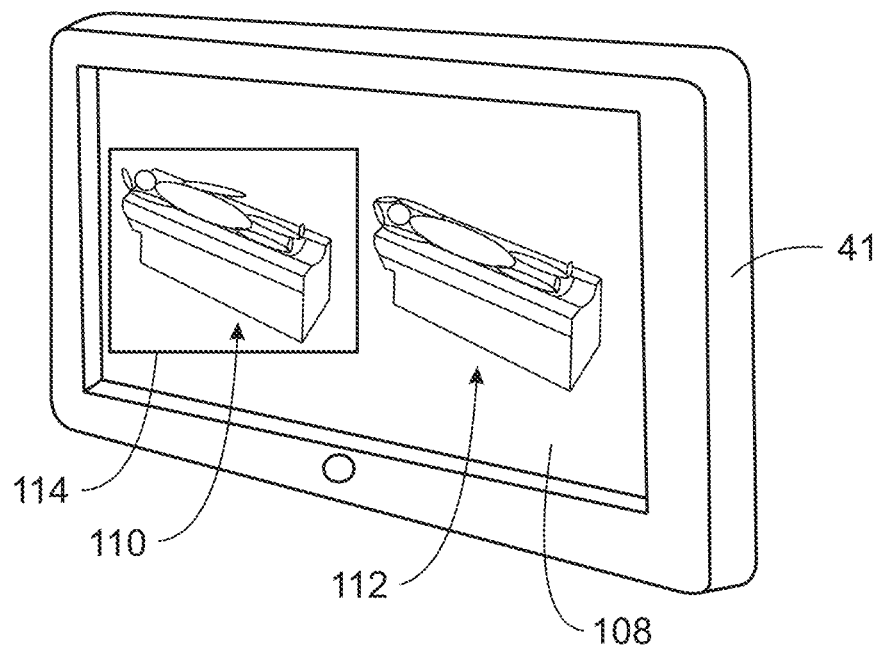
FIG. 8 is a schematic diagram of a screen on the external display of the CT imaging system providing positioning guidance (with the patient in a second incorrect position), in accordance with aspects of the present disclosure.
Figure 9:
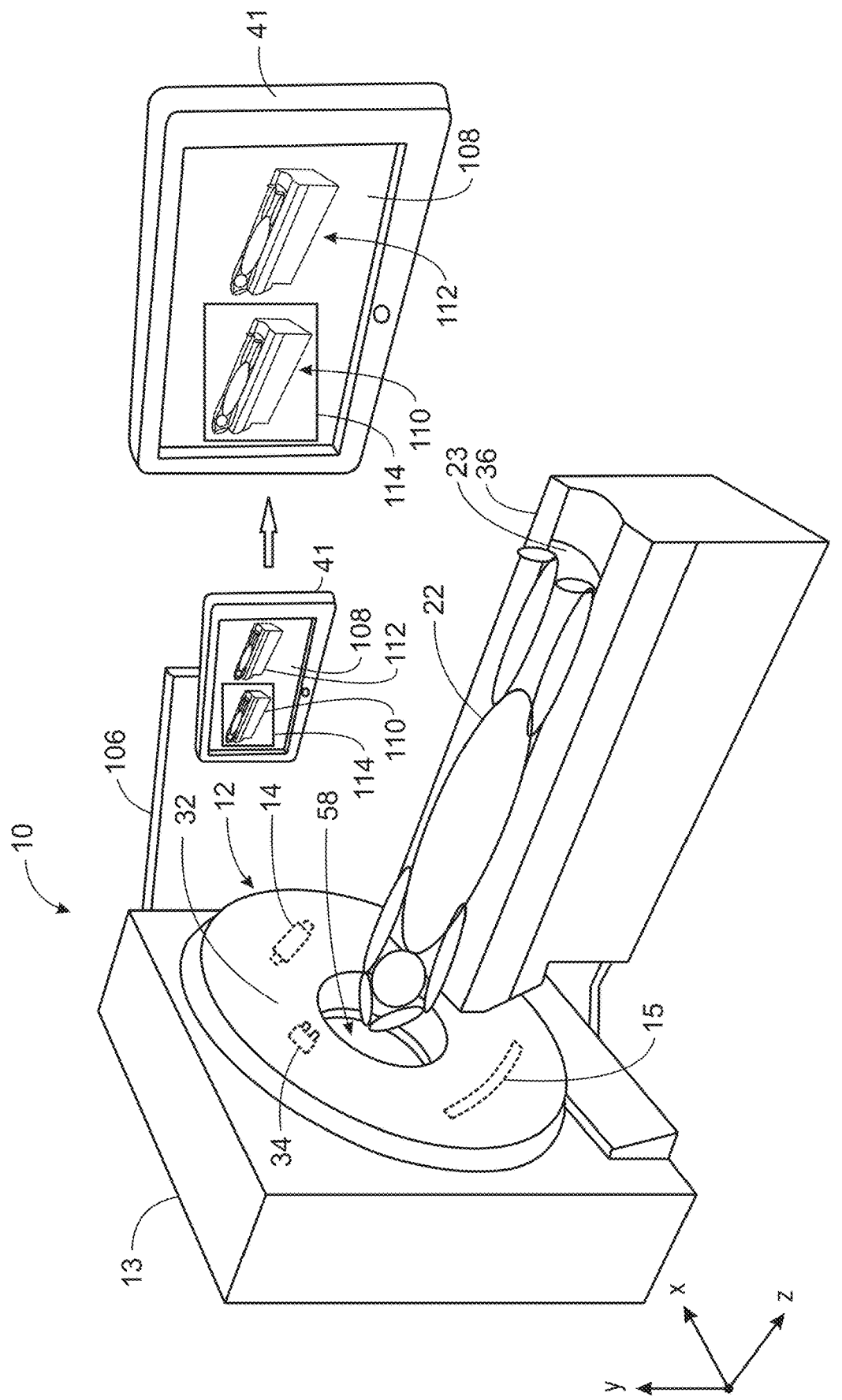
FIG. 9 is a schematic diagram of the CT imaging system in FIG. 6 displaying a current position and a target position of the patient (with the patient in a correct position), in accordance with aspects of the present disclosure.

FIGS. 7 and 8 are schematic diagrams of the screen 108 on the external display 41 of the CT imaging system 10 providing positioning guidance. In FIGS. 7 and 8, rendering 110 shown on the screen illustrates the multi-dimensional avatar of the patient on the cradle in the current (real time) position. The image 112 representing the multi-dimensional avatar of the patient disposed on the cradle in the target position is shown alongside the rendering 110 on the screen 108. Rendering 110 in FIG. 7 shows the current position of the patient (via the multi-dimensional avatar) is incorrect relative to the target position. Rendering 110 in FIG. 8 shows the current position of the patient (via the multi-dimensional avatar) is incorrect relative to the target position. In FIGS. 7 and 8, a shape 114 (e.g., box) is disposed about the rendering 110. In certain embodiments, the shape 114 is color coded. For example, since the current position of the patient is incorrect the shape 114 in FIGS. 7 and 8 may be shown in first color (e.g., red) to indicate the incorrect position. The shape 114 being in a second color (e.g., green) different from the first color indicates that the position of patient is correct (i.e., matches the target position). In FIG. 9, the patient 22 is positioned correctly. As a result, the shape 114 disposed about the rendering 110 on the screen 108 is colored the second color (e.g., green) to indicate that the position of the patient 22 is correct.

Figure 10:
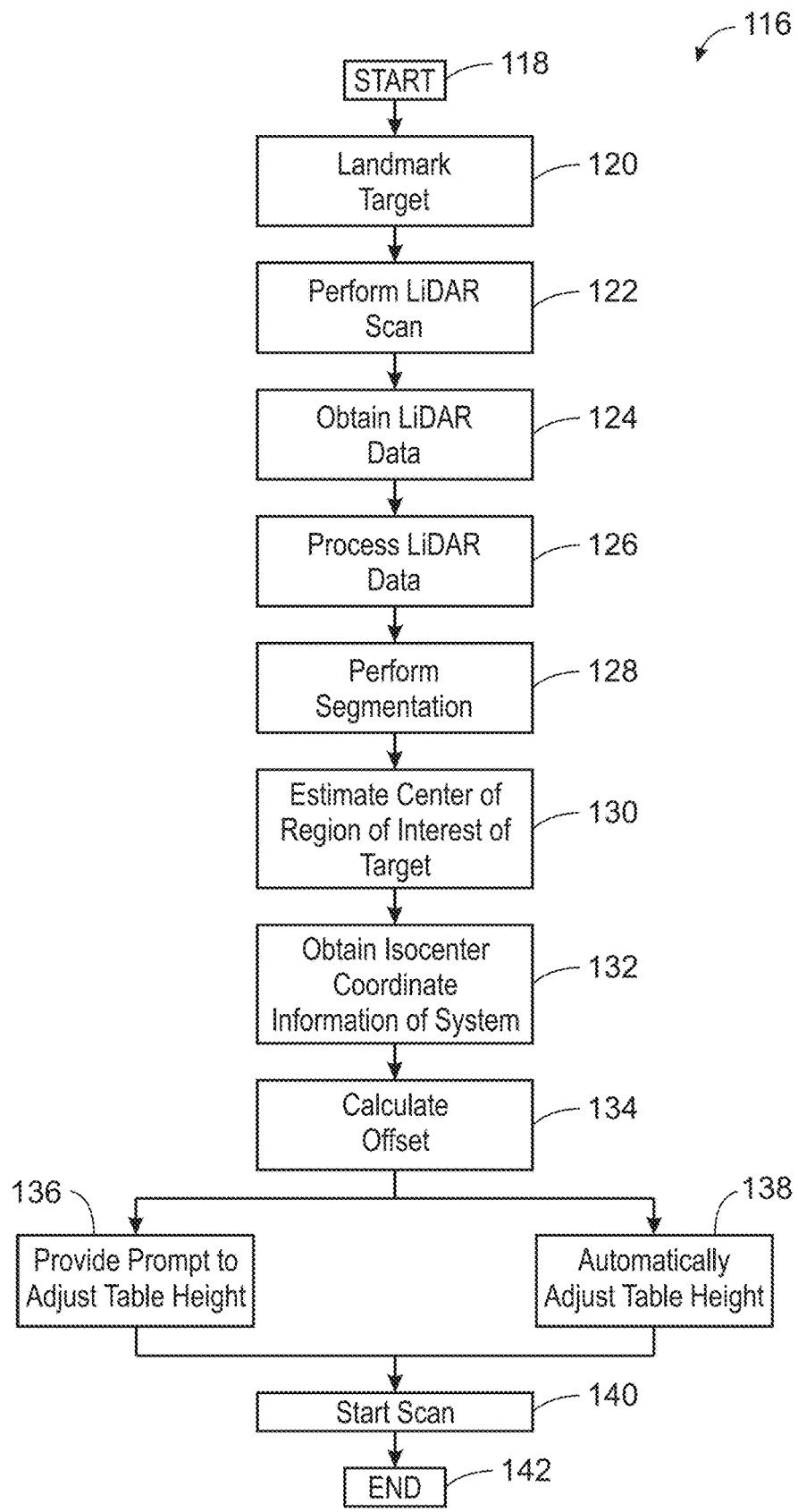
FIG. 10 is a flowchart of a method for centering of a target for a scan, in accordance with aspects of the present disclosure.

FIG. 10 is a flowchart of a method 116 for centering of a target for a scan. The method 116 may be performed by one or more components (e.g., processing circuitry) of the LiDAR scanning system 32 and/or the CT imaging system 10 in FIGS. 1 and 2. One or more steps of the method 116 may be performed simultaneously and/or in a different order than depicted in FIG. 10.

Upon starting (block 118), the method 116 includes landmarking a target disposed on a cradle of a table of a CT imaging system outside the bore of the gantry (block 120). In certain embodiments, the target is a patient. In certain embodiments, the target is a phantom. The method 116 also includes performing a LiDAR scan on the target (block 122). The LiDAR scan is performed utilizing the LiDAR scanning system 32 described in FIGS. 1 and 2. The LiDAR scan is performed prior to a CT scan (e.g., calibration scan or diagnostic scan).

The method 116 also includes obtaining or receiving LiDAR data from the LiDAR scan (block 124). The LiDAR data represents light images of different views acquired at different angular positions (e.g., relative to axis of rotation 24 in FIG. 2). The method 116 further includes processing the LiDAR data (block 126). Processing the LiDAR includes combining the LiDAR data and generating 3D information (i.e., 3D measurement) such as 3D point cloud data of the target. Processing of the LiDAR data may also include changing a coordinate system, inspecting point components and values, tiling the LiDAR data, clipping points outside a defined boundary, reducing the number of points, splitting by component value, filtering the LiDAR data, and/or other processing techniques. These processing techniques may be performed prior to and/or after the generation of the 3D information.

The method 116 further includes performing segmentation on the 3D information (3D point cloud data) to generate 3D point cloud information of the target (block 128). In certain embodiments, the segmentation of the 3D information is performed utilizing density based spatial clustering of applications with noise (DBSCAN). The 3D point cloud information of the patient represents a high fidelity topography of the target.

The method 116 even further includes estimating a center of a region of interest of the target (block 130). Estimating the center of the region of interest may include setting landmarks as needed and isolating the region of interest from the segmented 3D information of the target. The isolated region of interest may be a two-dimensional (2D) contour representation for a selected surface of the region of interest. The center of region of interest may be determined from the 2D contour representation of the region of interest of the target. In certain embodiments, estimating the center of region of interest of the target includes estimating a center of mass attenuation of a region of interest of a patient. In this embodiment, upon isolating the region of interest (2D contour representation) a location of the region of interest may be determined from an anatomical model. The anatomical model may be utilized to estimate the center of the mass attenuation of the patient. In certain embodiments, the anatomical model is scaled using the LiDAR data.

The method 116 still further includes obtaining isocenter coordinate information from the CT imaging system (block 132). The isocenter coordinate information includes an isocenter of the gantry. The method 116 yet further includes calculating an offset between the center of the region of interest of the target and isocenter of the gantry (block 134).

In certain embodiments, the method 116 includes providing a prompt (e.g., on a console (e.g., display) of the CT imaging system) to the operator to adjust a height of the table by the determined offset to align the isocenter of the gantry with the center of region of interest of the target (block 136). In response, the processing circuitry receives an input to adjust the height of the table from the operator via an input device of the console. In certain, embodiments, the method 116 includes automatically moving the table (i.e., adjusting the height of the table) by the determined offset to align the isocenter of the gantry with the center of region of interest of the target (block 138). Adjusting the height of the table to align the isocenter of the gantry with the center of region of interest of the target (e.g., a patient) improves dose optimization.

Upon adjusting the table, the method 116 includes starting the scan (block 140). In certain embodiments, the scan is CT diagnostic scan of a patient. In certain embodiments, the scan is a CT calibration scan utilizing a phantom. Upon staring the scan (block 140), the method 116 ends (block 142).

Figure 11:
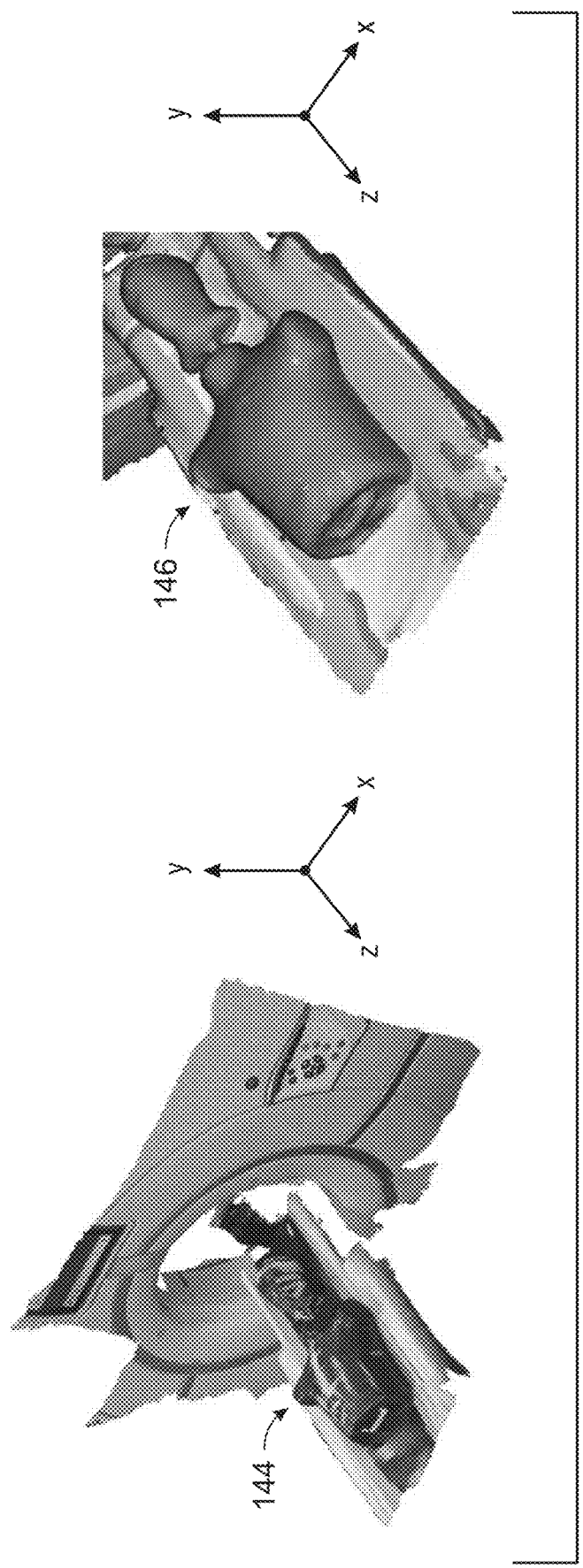
FIG. 11 is a schematic diagram illustrating a rendering of 3D LiDAR data obtained of a patient and a segmented representation of the 3D LiDAR data, in accordance with aspects of the present disclosure.

FIG. 11 is a schematic diagram illustrating a rendering of 3D LiDAR data obtained of a patient and a segmented representation of the 3D LiDAR data. On the left side of FIG. 11, a representation 144 of obtained 3D LiDAR data obtained of a patient on a table obtained by LiDAR scanning system (e.g., LiDAR scanning system 32 in FIGS. 1 and 2) prior to a scan of the patient. On the right side of FIG. 11, a representation 146 of segmented 3D LiDAR data. The representation 146 of the segmented 3D LiDAR data is obtained by performing 3D segmentation on the 3D LiDAR point cloud data. In certain embodiments, density based spatial clustering of applications with noise (DBSCAN) is utilized for performing the segmentation.

Figure 12:
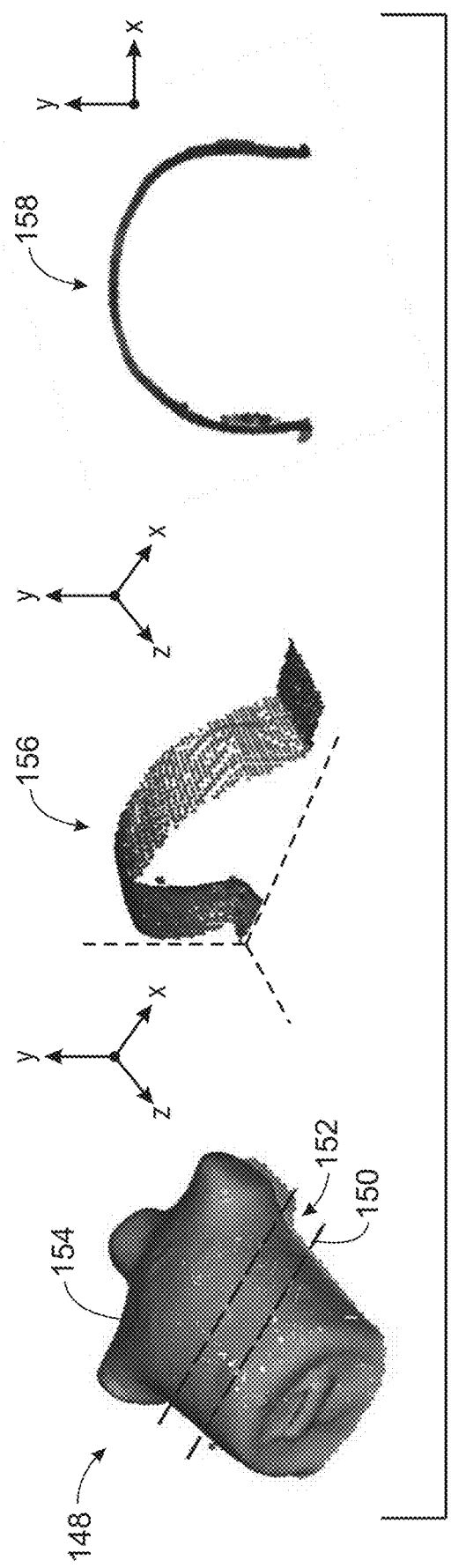
FIG. 12 is a schematic diagram of components for determining a center of a region of interest of a patient, in accordance with aspects of the present disclosure.

FIG. 12 is a schematic diagram of components for determining a center of a region of interest of a patient. Representation 148 represents the setting of a landmark 150 and isolating a region of interest 152 in the 3D segmented representation 154 of the patient obtained from 3D LiDAR point cloud data. Representation 156 represents an isolated point cloud (e.g., for the region of interest) for monitoring (i.e., determining a center). Representation 158 is a 2D contour representation for a selected surface of the region of interest from which the center is calculated.

Figure 13:
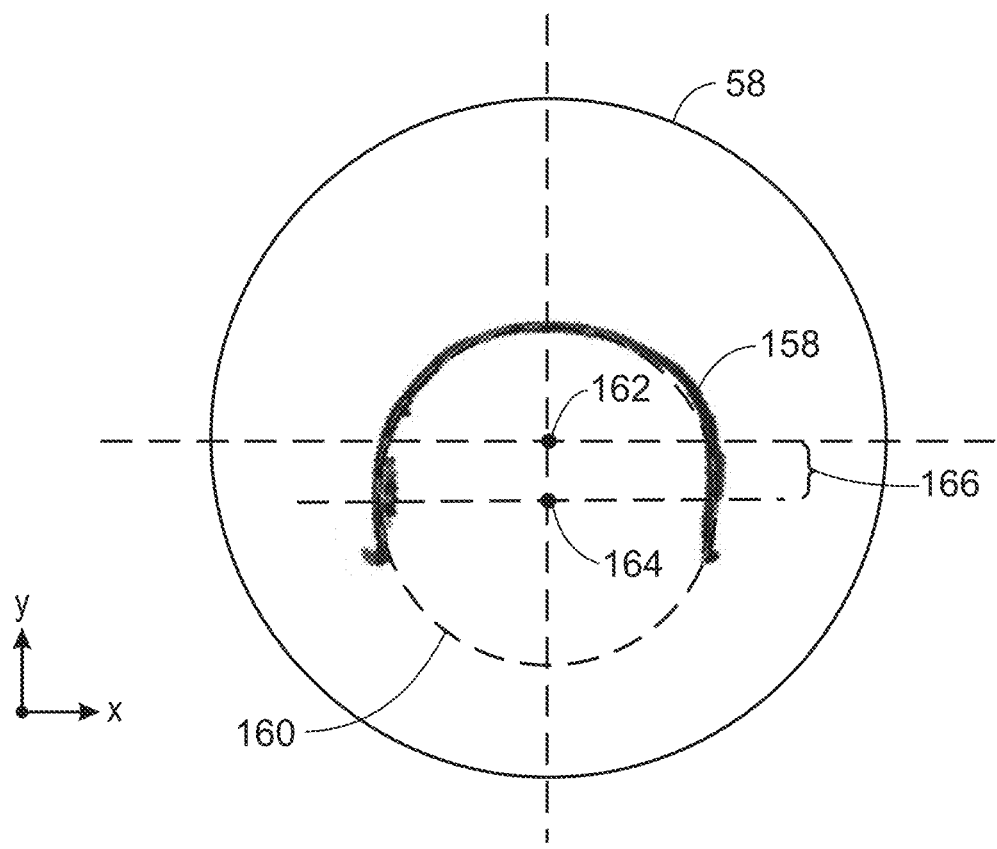
FIG. 13 is a schematic diagram illustrating an isocenter positioning offset calculation for an automated table height adjustment feature with a patient for a CT scan (e.g., diagnostic scan), in accordance with aspects of the present disclosure.

FIG. 13 is a schematic diagram illustrating an isocenter positioning offset calculation for an automated table height adjustment feature with a patient for a CT scan (e.g., diagnostic scan). As depicted in FIG. 13, the 2D contour representation 158 for the selected surface of region of interest of the patient is shown relative to a bore 58 of the gantry from an axial end. As depicted in FIG. 13, a fitting line 160 is applied to the 2D contour representation 158. Point 162 represents an isocenter of the gantry. Point 164 represents a calculated center of region of interest of the patient. As depicted in FIG. 13, an offset 166 is calculated between the isocenter 162 of the gantry and the calculated center 164 of the region of interest of the patient. As discussed above, the offset 166 is utilized to adjust (e.g., automatically) a height of the table for a scan (e.g., CT diagnostic scan) of the patient.

Figure 14:
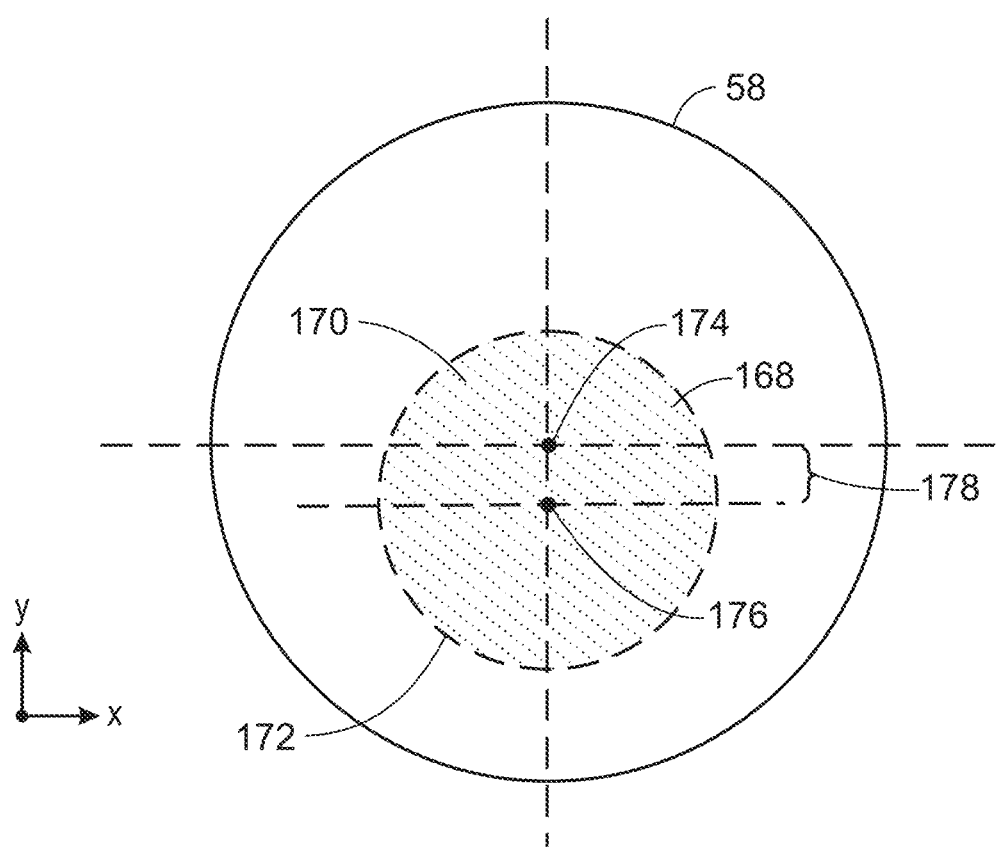
FIG. 14 is a schematic diagram illustrating an isocenter positioning offset calculation for an automated table height adjustment feature with a phantom for a CT calibration scan.

FIG. 14 is a schematic diagram illustrating an isocenter positioning offset calculation for an automated table height adjustment feature with a phantom for a CT calibration scan. As depicted in FIG. 14, a 2D contour representation 168 for the selected surface of region of interest of a phantom 170 is shown relative to a bore 58 of the gantry from an axial end. In certain embodiments, the phantom 170 is placed on the table. In certain embodiments, the phantom 170 is attached with the table using a phantom holder. As depicted in FIG. 14, a fitting line 172 is applied to the 2D contour representation 168. Point 174 represents an isocenter of the gantry. Point 176 represents a calculated center of region of interest of the phantom 170. As depicted in FIG. 14, an offset 178 is calculated between the isocenter 174 of the gantry and the calculated center 176 of the region of interest of the phantom 170. As discussed above, the offset 178 is utilized to adjust (e.g., automatically) a height of the table for a scan (e.g., CT calibration scan) of the phantom 170.

Figure 15:
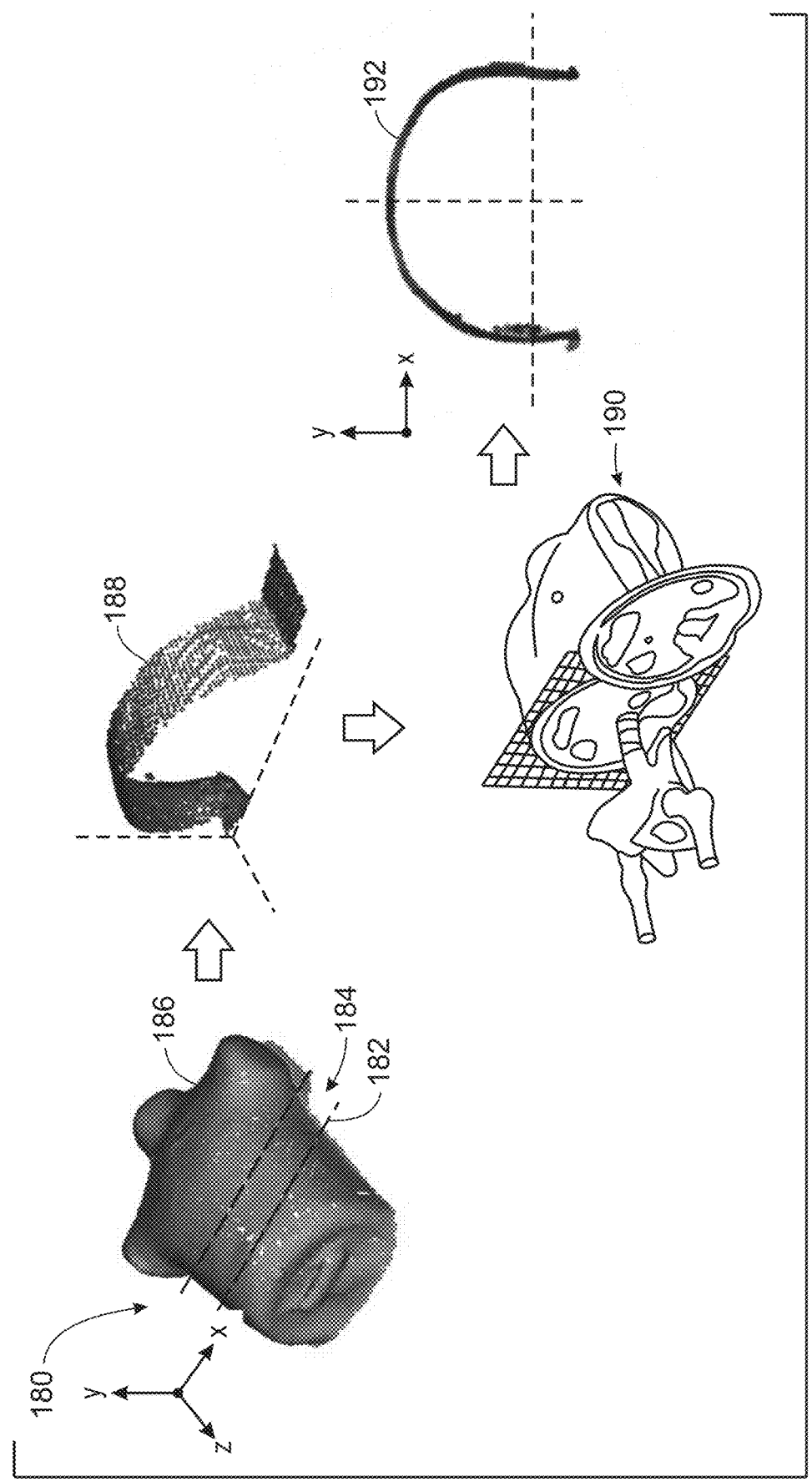
FIG. 15 is a schematic diagram of components for determining a mass attenuation center of a region of interest of a patient, in accordance with aspects of the present disclosure.

FIG. 15 is a schematic diagram of components for determining a mass attenuation center of a region of interest of a patient. Representation 180 represents the setting of a landmark 182 and isolating a region of interest 184 in the 3D segmented representation 186 of the patient obtained from 3D LiDAR point cloud data. Representation 188 represents an isolated point cloud (e.g., for the region of interest) for monitoring (i.e., determining a center). In certain embodiments, estimating the center of region of interest of the target includes estimating a center of mass attenuation of a region of interest of a patient. As depicted in FIG. 15, upon isolating the region of interest (i.e., the isolated point cloud 188, a location of the region of interest may be determined from an anatomical model as indicate by reference numeral 190. The anatomical model 190 may be utilized to estimate the center of the mass attenuation of the patient. In certain embodiments, the anatomical model 190 is scaled using the LiDAR data. Representation 192 is a 2D contour representation for a selected surface of the region of interest from which the center of mass attenuation is calculated.

Technical effects of the disclosed embodiments include providing a LiDAR guided patient positioning apparatus that guides and assists the subject to position themselves for a CT scan. In particular, the LiDAR-based data is utilized to guide a subject within an interactive virtual visual apparatus to improve overall efficiency and the robustness of the workflow in utilizing a CT scanner. The LiDAR-based data generates high-fidelity positional 3D data without any marker or pattern projected on the subject. Thus, data can be collected effortlessly and the 3D point cloud information can be efficiently used to improve the robustness of the CT data acquisition workflow process. This also enables the technologist to be out of the scan room during patient positioning, thus, reducing the potential spread of any contagious disease the subject may have. Technical effects of the automated table adjustment feature also ensures dose optimization and automated phantom adjustment during calibration. Technical effects of the disclosed embodiments provide for effortless, efficient workflow and/or dose optimization.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
a computed tomography (CT) imaging system, comprising:
a gantry having a bore, rotatable about an axis of rotation;
a table having a cradle and configured to move a subject to be imaged into and out of the bore of the gantry;
a radiation source mounted on the gantry and configured to emit an X-ray beam; and
a detector configured to detect the X-ray beam emitted by the radiation source;
a display disposed adjacent the table within view of the subject;
a light detection and ranging (LiDAR) scanning system physically coupled to the CT imaging system, wherein the LiDAR scanning system is configured to acquire data of the subject from different angular positions relative to the axis of rotation when the subject is disposed on the cradle; and
processing circuitry configured to receive the data acquired with the LiDAR scanning system, to generate a multi-dimensional avatar of the subject representing a topography of the subject, to cause display of the multi-dimensional avatar positioned on the cradle that represents a current position of the subject on the display, and to provide instructions on the display to enable the subject to guide themselves to a target position on the cradle for a CT scan with the CT imaging system.

2. The medical imaging system of claim 1, wherein the processing circuitry is configured to provide the instructions by causing display of the multi-dimensional avatar in the target position positioned on the cradle on the display alongside the multi-dimensional avatar positioned on the cradle in the current position.

3. The medical imaging system of claim 2, wherein the processing circuitry is further configured to perform template matching between the current position of the subject and the target position.

4. The medical imaging system of claim 3, wherein the processing circuitry is further configured to provide a user-perceptible indication as to whether the current position of the subject and the target position match.

5. The medical imaging system of claim 4, wherein the user-perceptible indication is provided via color coding of a shape on the display disposed around the multi-dimensional avatar positioned on the cradle in the current position, and wherein the shape is displayed in a first color when the current position of the subject and the target position match, and the shape is displayed in a second color different from the first color when the current position of the subject and the target position do not match.

6. The medical imaging system of claim 4, wherein user-perceptible indication is a directional arrow shown on the display to assist to the subject to achieve the target position.

7. The medical imaging system of claim 4, wherein the processing circuitry is further configured to provide additional instructions to the subject to hold the current position for the CT scan when the current position of the subject and the target position match.

8. The medical imaging system of claim 1, wherein the processing circuitry is further configured to determine the target position based on a scan protocol for the CT scan.

9. The medical imaging system of claim 1, wherein the display is coupled to the gantry.

10. A computer-implemented method, comprising:
receiving, at a processor, data acquired with a light detection and ranging (LiDAR) scanning system physically coupled to a computed tomography (CT) imaging system of a subject to be imaged disposed on a cradle of a table, wherein the table is configured to move the subject into and out of a bore of a gantry of the CT imaging system;
generating, via the processor, a multi-dimensional avatar of the subject representing a topography of the subject;
causing, via the processor, display of the multi-dimensional avatar positioned on the cradle that represents a current position of the subject on a display, wherein the display is disposed adjacent the table within view of the subject; and
providing, via the processor, instructions on the display to enable the subject to guide themselves to a target position on the cradle for a CT scan with the CT imaging system.

11. The computer-implemented method of claim 10, wherein providing the instructions comprises causing display of the multi-dimensional avatar in the target position positioned on the cradle on the display alongside the multi-dimensional avatar positioned on the cradle in the current position.

12. The computer-implemented method of claim 11, further comprising performing, via the processor, template matching between the current position of the subject and the target position.

13. The computer-implemented method of claim 12, further comprising providing, via the processor, a user-perceptible indication as to whether the current position of the subject and the target position match.

14. The computer-implemented method of claim 13, wherein the user-perceptible indication is provided via color coding of a shape on the display disposed around the multi-dimensional avatar positioned on the cradle in the current position.

15. The computer-implemented method of claim 14, wherein the shape is displayed in a first color when the current position of the subject and the target position match, and the shape is displayed in a second color different from the first color when the current position of the subject and the target position do not match.

16. The computer-implemented method of claim 13, further comprising providing, via the processor, additional instructions to the subject to hold the current position for the CT scan when the current position of the subject and the target position match.

17. A non-transitory computer-readable medium, the computer-readable medium comprising processor-executable code that when executed by a processor, causes the processor to:

receive data acquired with a light detection and ranging (LiDAR) scanning system physically coupled to a computed tomography (CT) imaging system of a subject to be imaged disposed on a cradle of a table, wherein the table is configured to move the subject into and out of a bore of a gantry of the CT imaging system;

generate a multi-dimensional avatar of the subject representing a topography of the subject;

cause display of the multi-dimensional avatar positioned on the cradle that represents a current position of the subject on a display, wherein the display is disposed adjacent the table within view of the subject; and provide instructions on the display to enable the subject to guide themselves to a target position on the cradle for a CT scan with the CT imaging system.

18. The non-transitory computer-readable medium of claim 17, wherein providing the instructions comprises causing display of the multi-dimensional avatar in the target position positioned on the cradle on the display alongside the multi-dimensional avatar positioned on the cradle in the current position.

19. The non-transitory computer-readable medium of claim 18, wherein the processor-executable code, when executed by the processor, further causes the processor to perform template matching between the current position of the subject and the target position.

20. The non-transitory computer-readable medium of claim 19, wherein the processor-executable code, when executed by the processor, further causes the processor to provide a user-perceptible indication as to whether the current position of the subject and the target position match.

* * * * *